(12) United States Patent
Litvak et al.

(10) Patent No.: US 9,486,630 B2
(45) Date of Patent: Nov. 8, 2016

(54) ELECTRO-ACOUSTIC STIMULATION SYSTEMS THAT PERFORM PREDETERMINED ACTIONS IN ACCORDANCE WITH EVOKED RESPONSES

(71) Applicant: ADVANCED BIONICS AG, Staefa (CH)

(72) Inventors: Leonid M. Litvak, Los Angeles, CA (US); Smita S. Agrawal, Stevenson Ranch, CA (US); Gulamali Emadi, Van Nuys, CA (US); Aniket Saoji, Newhall, CA (US); Charles C. Finley, Stevenson Ranch, CA (US); R. Tissa Karunasiri, Valencia, CA (US); Kanthaiah Koka, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/386,331

(22) PCT Filed: Mar. 22, 2013

(86) PCT No.: PCT/US2013/033605
§ 371 (c)(1),
(2) Date: Sep. 18, 2014

(87) PCT Pub. No.: WO2013/142844
PCT Pub. Date: Sep. 26, 2013

(65) Prior Publication Data
US 2015/0057714 A1 Feb. 26, 2015

Related U.S. Application Data

(60) Provisional application No. 61/614,129, filed on Mar. 22, 2012.

(51) Int. Cl.
*A61N 1/36* (2006.01)
*A61B 5/04* (2006.01)
(Continued)

(52) U.S. Cl.
CPC ....... *A61N 1/36032* (2013.01); *A61B 5/04001* (2013.01); *A61B 5/121* (2013.01);
(Continued)

(58) Field of Classification Search
CPC .......................... A61B 5/04001; A61B 5/121
See application file for complete search history.

(56) References Cited

U.S. PATENT DOCUMENTS

| | | |
|---|---|---|
| 5,776,179 A | 7/1998 | Ren et al. |
| 6,754,537 B1 * | 6/2004 | Harrison et al. ............... 607/57 |

(Continued)

FOREIGN PATENT DOCUMENTS

| | | |
|---|---|---|
| WO | WO-97/09863 | 3/1997 |
| WO | WO-2009/124165 | 10/2009 |

OTHER PUBLICATIONS

International Search Report and Written Opinion received in International Application No. PCT/US13/033607, dated May 31, 2013.

(Continued)

*Primary Examiner* — Carl H Layno
*Assistant Examiner* — Jennifer Ghand
(74) *Attorney, Agent, or Firm* — ALG Intellectual Property, LLC

(57) ABSTRACT

An exemplary system includes 1) an electro-acoustic stimulation ("EAS") sound processor configured to be located external to a patient, 2) a cochlear implant communicatively coupled to the EAS sound processor and configured to be implanted within the patient, 3) an electrode array communicatively coupled to the cochlear implant and configured to be located within a cochlea of the patient, and 4) a receiver communicatively coupled to the EAS sound processor and configured to be in communication with an ear of the patient. The EAS sound processor directs at least one of the cochlear implant and the receiver to apply stimulation to the patient, records an evoked response that occurs in response to the stimulation, and performs a predetermined action in accordance with the evoked response. Corresponding systems and methods are also disclosed.

20 Claims, 10 Drawing Sheets

(51) Int. Cl.
- A61B 5/12 (2006.01)
- A61N 1/05 (2006.01)
- H04R 25/00 (2006.01)
- A61N 1/372 (2006.01)
- H04R 1/10 (2006.01)

(52) U.S. Cl.
CPC ....... A61N 1/0541 (2013.01); A61N 1/37247 (2013.01); H04R 1/1008 (2013.01); H04R 25/00 (2013.01); H04R 25/606 (2013.01); H04R 25/70 (2013.01); H04R 2225/67 (2013.01); H04R 2460/03 (2013.01)

(56) References Cited

U.S. PATENT DOCUMENTS

| | | | |
|---|---|---|---|
| 7,561,920 B2* | 7/2009 | Faltys et al. | 607/57 |
| 8,086,319 B2 | 12/2011 | van Dijk | |
| 8,244,365 B2 | 8/2012 | Dijk et al. | |
| 8,521,297 B2 | 8/2013 | Polak | |
| 9,155,886 B2 | 10/2015 | James et al. | |
| 2004/0152946 A1* | 8/2004 | Franck | 600/25 |
| 2005/0261748 A1 | 11/2005 | van Dijk | |
| 2007/0135862 A1 | 6/2007 | Nicolai et al. | |
| 2008/0249589 A1 | 10/2008 | Cornejo Cruz et al. | |
| 2008/0319508 A1* | 12/2008 | Botros et al. | 607/57 |
| 2009/0240307 A1* | 9/2009 | Seligman | A61N 1/36032 607/57 |
| 2009/0254149 A1 | 10/2009 | Polak | |
| 2009/0259140 A1 | 10/2009 | Buchman | |
| 2010/0030012 A1 | 2/2010 | Meskens | |
| 2010/0145411 A1 | 6/2010 | Spitzer | |
| 2010/0198301 A1 | 8/2010 | Smith | |
| 2011/0082521 A1* | 4/2011 | Botros et al. | 607/57 |

OTHER PUBLICATIONS

International Search Report and Written Opinion received in International Application No. PCT/US13/033605, dated Jul. 1, 2013.
International Search Report and Written Opinion received in International Application No. PCT/US13/033604, dated Jul. 1, 2013.
Miller, Charles A., et al., "Auditory Nerve Fiber Responses to Combined Acoustic and Electric Stimulation", *Journal of the Association for Research in Otolaryngology*, Springer-Verlag, NE, vol. 10, No. 3, Feb. 10, 2009, pp. 425-445.
Payton, Lin et al., "Ipsilateral Masking Between Acoustic and Electric Stimulations", *The Journal of the Acoustical Society of America, American Institute of Physics for the Acoustical Society of America*, New York, NY, US, vol. 130, No. 2, Aug. 1, 2011, pp. 858-865.
Davis, "An Active Process in Cochlear Mechanics", *Hearing Research*, 9 (1983) 79-90, Elsevier Biomedical Press.
Kohlloffel, "Longitudinal Amplitude and Phase Distribution of the Cochlear Microphonic (Guinea Pig) and Spatial Filtering", *J. Sound Vib.* (1970) 11 (3), 325-334.
Tasaki, et al., "The Space-Time Pattern of the Cochlear Microphonics (Guinea Pig), as Recorded by Differential Electrodes", *The Journal of the Acoustical Society of America*, vol. 24, No. 5, Sep. 1952.
Non-Final Office Action received in U.S. Appl. No. 14/386,330 dated Dec. 7, 2015.
Final Office Action received in U.S. Appl. No. 14/386,735 dated Jan. 20, 2016.

* cited by examiner

ELECTRO-ACOUSTIC STIMULATION SYSTEMS THAT PERFORM PREDETERMINED ACTIONS IN ACCORDANCE WITH EVOKED RESPONSES

RELATED APPLICATIONS

The present application claims priority to U.S. Provisional Patent Application No. 61/614,129, filed on Mar. 22, 2012, and entitled "Methods and Systems for Fitting an Electro-acoustic Stimulation System to a Patient," the contents of which are hereby incorporated by reference in their entirety.

BACKGROUND INFORMATION

Many hearing loss patients have some degree of residual hearing in the low frequencies (e.g., below 1 kHz) and a severe hearing loss in the high frequencies (e.g., above 1 kHz). These people cannot benefit from traditional hearing aid amplification because of the severity of the hearing loss in the high frequencies. Nor are they classic cochlear implant candidates, because of their mostly intact low frequency residual hearing.

For this group of people, electro-acoustic stimulation ("EAS") systems have been developed that provide such patients with the ability to perceive both low and high frequencies. Electro-acoustic stimulation combines the functionality of a hearing aid and a cochlear implant together in the same ear by providing acoustic stimulation representative of low frequency audio content and electrical stimulation representative of high frequency content. The auditory nerve combines the acoustic and electric stimuli into one auditory signal. Results of various studies have shown that electro-acoustic stimulation may enhance speech understanding, pitch discrimination, and music appreciation.

The effectiveness of an EAS system may be affected by a number of different factors. For example, surgical complications (e.g., a misalignment of an electrode array within the cochlea, destruction of hair cells during implantation of a cochlear implant, etc.) and post-surgery complications (e.g., residual hearing loss, wax buildup in the ear, infections, and component failure) may be detrimental to EAS system performance. Unfortunately, many of these factors are not readily discernible, thereby making it difficult or impossible to account for them (e.g., by adjusting one or more control parameters governing an operation of the EAS system). Hence, a patient may unknowingly suffer from sub-optimal EAS system performance.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
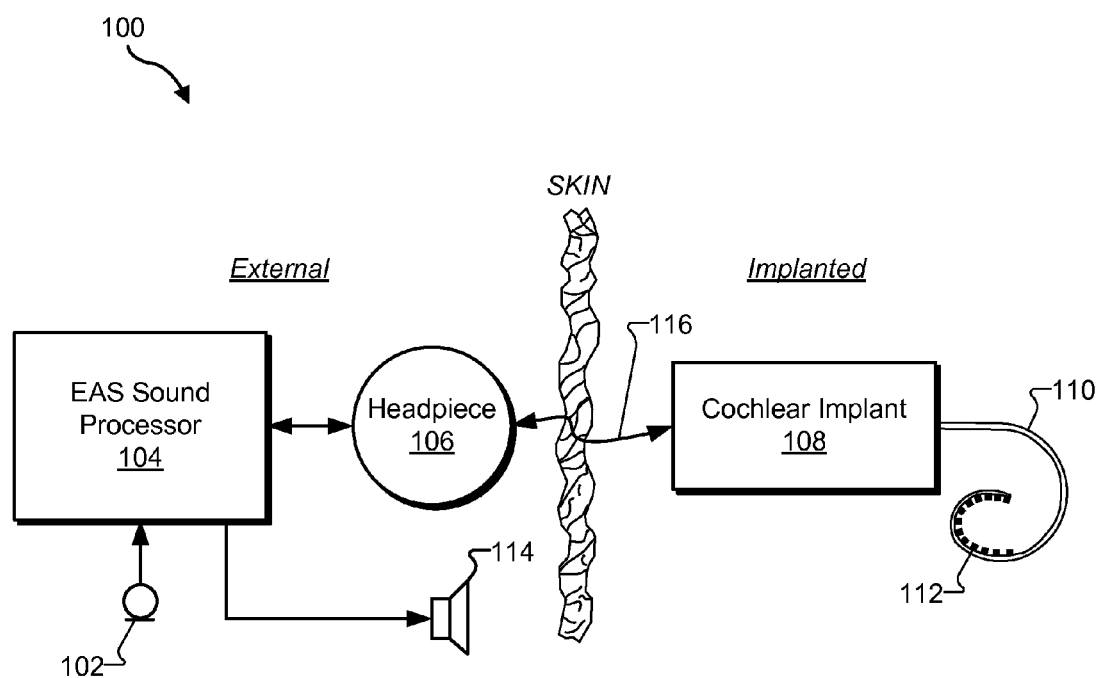
FIG. 1 illustrates an exemplary EAS system according to principles described herein.

EAS systems that elicit and record evoked responses (e.g., neural responses and/or cochlear responses) and perform predetermined actions in accordance with the evoked responses are described herein. As will be described below, an exemplary EAS system may include 1) an EAS sound processor configured to be located external to a patient, 2) a cochlear implant communicatively coupled to the EAS sound processor and configured to be implanted within the patient, 3) an electrode array communicatively coupled to the cochlear implant and configured to be located within a cochlea of the patient, and 4) a receiver communicatively coupled to the EAS sound processor and configured to be in communication with an ear of the patient. In some examples, the EAS sound processor directs at least one of the cochlear implant and the receiver to apply stimulation to the patient, records an evoked response that occurs in response to the stimulation, and performs a predetermined action in accordance with the evoked response.

For example, the EAS sound processor may direct the cochlear implant to apply electrical stimulation by way of at least one electrode included in the electrode array and/or the receiver to apply acoustic stimulation to the patient. The EAS sound processor may then record an evoked response that occurs in response to the electrical and/or acoustic stimulation and compare the evoked response to a baseline response and/or one or more previously recorded evoked responses. If the evoked response differs from the baseline response and/or the one or more previously recorded evoked responses (e.g., if the evoked response is not within a predetermined range of the baseline response and/or the one or more previously recorded evoked responses), the EAS sound processor may adjust one or more control parameters governing an operation of the EAS sound processor, notify the patient and/or another user of the potentially problematic evoked response, and/or take any other suitable action as may serve a particular implementation. These and other examples will be described in more detail below.

By eliciting an evoked response and then performing one or more predetermined actions in accordance with the evoked response, the systems and methods described herein may facilitate optimal performance of the EAS system, assist in evaluating one or more conditions (e.g., a residual hearing status) of the patient, and/or otherwise provide benefit to the patient.

As used herein, an "evoked response" may include any type of cochlear response and/or neural response. Exemplary cochlear responses include, but are not limited to, cochlear microphonics, summating potentials, otoacoustic emissions, etc. Exemplary neural responses include, but are not limited to, auditory nerve responses, brainstem responses, compound action potentials, frequency following responses, etc. An evoked response may additionally or alternatively include a stapedius response and/or any other type of response that may occur in response to application of electrical and/or acoustic stimulation by an EAS system.

Additional or alternative manners in which an evoked response may be elicited are described in more detail in co-pending PCT Application No. PCT/US2013/033607, entitled "Programming Systems for Eliciting Evoked Responses in a Cochlear Implant Patient and Performing Predetermined Actions in Accordance with the Evoked Responses," filed the same day as the present application, and incorporated herein by reference in its entirety.

FIG. 1 illustrates an exemplary EAS system 100. EAS system 100 may include a microphone 102, an EAS sound processor 104, a headpiece 106 having a coil disposed therein, a cochlear implant 108, an electrode array 110 with a plurality of electrodes 112 disposed thereon, and a receiver 114 (also referred to as a "loudspeaker"). Additional or alternative components may be included within EAS system 100 as may serve a particular implementation.

As shown, various components of EAS system 100 may be located external to the patient including, but not limited to, microphone 102, EAS sound processor 104, headpiece 106, and receiver 114. Various components of EAS system 100 may be implanted within the patient including, but not limited to, cochlear implant 108 and electrode array 110. As will be described in more detail below, additional or alternative components may be included within EAS system 100 as may serve a particular implementation. The components shown in FIG. 1 will now be described in more detail.

Microphone 102 may be configured to detect audio signals (i.e., audio content) presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to EAS sound processor 104. Additionally or alternatively, microphone 102 may be implemented by one or more microphones disposed within headpiece 106, one or more microphones disposed within EAS sound processor 104, and/or any other suitable microphone as may serve a particular implementation.

EAS sound processor 104 (i.e., one or more components included within EAS sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, EAS sound processor 104 may process the one or more audio signals in accordance with a selected sound processing strategy or program to generate appropriate stimulation parameters for controlling cochlear implant 108. EAS sound processor 104 may include or be implemented by a behind-the-ear ("BTE") unit, a body worn device, and/or any other sound processing unit as may serve a particular implementation.

In some examples, EAS sound processor 104 may wirelessly transmit stimulation parameters (e.g., in the form of data words included in a forward telemetry sequence) and/or power signals to cochlear implant 108 by way of a wireless communication link 116 between headpiece 106 and cochlear implant 108. It will be understood that communication link 116 may include a bi-directional communication link and/or one or more dedicated uni-directional communication links.

EAS sound processor 104 may be further configured to direct receiver 114 to apply acoustic stimulation representative of audio content to the patient. This may be performed in any suitable manner.

In some examples, EAS system 100 may be used when the patient has some residual hearing in the low frequencies (e.g., below 1000 Hz) and severe hearing loss in the high frequencies (e.g., above 1000 Hz). To this end, EAS sound processor 104 may direct cochlear implant 108 to apply electrical stimulation representative of audio content included in a relatively high frequency band (e.g., above 1000 Hz) to one or more stimulation sites within the patient (e.g., within the cochlea of the patient) by way of one or more electrodes 112 included in electrode array 110 and receiver 114 to apply acoustic stimulation representative of audio content included in a relatively low frequency band (e.g., below 1000 Hz) to the patient. In some alternative embodiments, the patient may have non-contiguous frequency regions of residual hearing. For example, the patient may have non-contiguous regions of damaged outer hair cells, which may result in the patient having residual hearing in non-adjacent frequency bands. EAS system 100 may also be used for these types of patients.

Headpiece 106 may be communicatively coupled to EAS sound processor 104 and may include an external antenna (e.g., a coil and/or one or more wireless communication components) configured to facilitate selective wireless coupling of EAS sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between EAS sound processor 104 and cochlear implant 108 via a communication link 116 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of implant that may be implanted within a patient and configured to apply stimulation to one or more stimulation sites located along an auditory pathway of a patient.

In some examples, cochlear implant 108 may be configured to generate electrical stimulation representative of an audio signal processed by EAS sound processor 104 (e.g., an audio signal detected by microphone 102) in accordance with one or more stimulation parameters transmitted thereto by EAS sound processor 104. To this end, cochlear implant 108 may include one or more current generators. In some examples, cochlear implant 108 may include one or more lock-in amplifiers. A lock-in amplifier allows for a relatively high signal-to-noise ratio when the expected phase and waveform of the evoked response is known ahead of time.

Cochlear implant 108 may be further configured to apply the electrical stimulation to one or more stimulation sites within the patient via one or more electrodes 112 disposed along electrode array 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
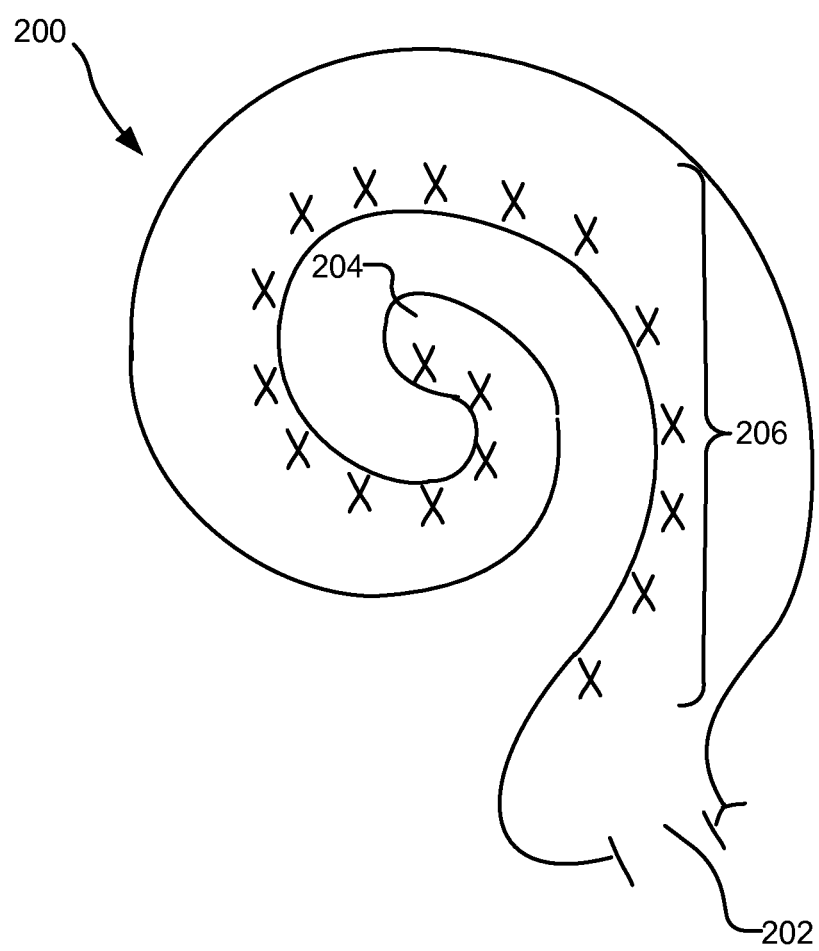
FIG. 2 illustrates a schematic structure of the human cochlea according to principles described herein.

FIG. 2 illustrates a schematic structure of the human cochlea 200 into which electrode array 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the lead, the anatomy of the patient's cochlea, and/or any other factor as may serve a particular implementation.

Returning to FIG. 1, receiver 114 may be communicatively coupled to EAS sound processor 104 and may be configured to be in communication with an ear of the patient. For example, receiver 114 may be integrated into an earmold configured to be located within the outer ear of the patient. The earmold may include any type of earmold that may be at least partially disposed within the outer ear of the patient. For example, the earmold may include an open dome configured to allow the ear to remain partially open (e.g., an open dome tip made from a soft silicone material and configured to resemble a tulip or flower bud), a closed dome configured to entirely close off the ear canal, a foam dome, and/or any other type of dome as may serve a particular implementation. As will be described in more detail below, receiver 114 may be configured to apply acoustic stimulation to the patient.

Figure 3:
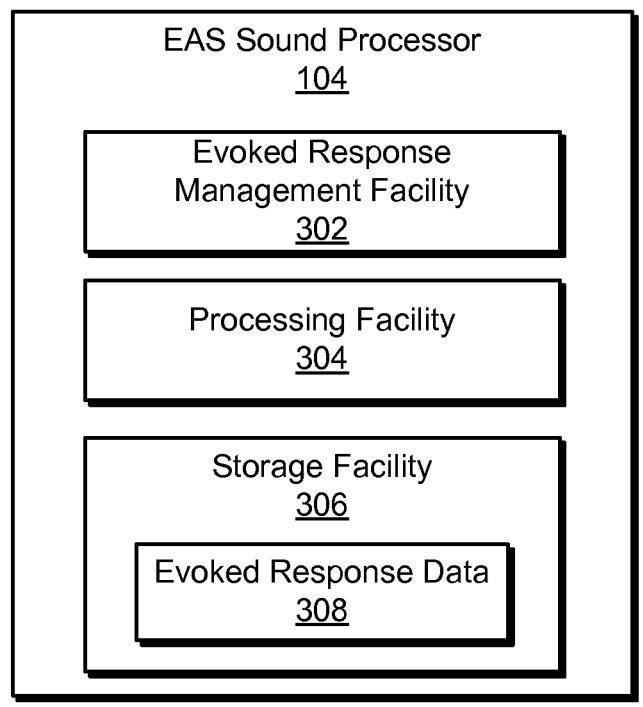
FIG. 3 illustrates exemplary components of an EAS sound processor according to principles described herein.

FIG. 3 illustrates exemplary components of EAS sound processor 104. As shown in FIG. 3, EAS sound processor 104 may include an evoked response management facility 302, a processing facility 304, and a storage facility 306, which may be in communication with one another using any suitable communication technologies. One or more of facilities 302-306 may include one or more computing devices and/or processors configured to perform one or more of the functions described herein. Facilities 302-306 will now be described in more detail.

Evoked response management facility 302 may be configured to perform one or more evoked response management operations. For example, evoked response management facility 302 may be configured to attempt to elicit an evoked response within a patient. This may be performed in any suitable manner. For example, evoked response management facility 302 may direct cochlear implant 108 and/or receiver 114 to apply stimulation to the patient and then determine whether an evoked response occurs in response to the stimulation. The presence or absence of an evoked response may be indicative of one or more conditions (e.g., a residual hearing status of the patient, auditory neuropathy, etc.).

Evoked response management facility 302 may direct cochlear implant 108 and/or receiver 114 to apply stimulation to the patient in any suitable manner. For example, evoked response management facility 302 may direct cochlear implant 108 to apply electrical stimulation to the patient by way of at least one electrode 112 included in electrode array 110. The electrical stimulation may have any suitable characteristic. For example, the electrical stimulation may include monopolar stimulation. The electrode to which the electrical stimulation is applied may be any electrode located within the cochlea of the patient (e.g., the most apical electrode included in electrode array 110).

As another example, evoked response management facility 302 may direct receiver 114 to apply acoustic stimulation to the patient. The acoustic stimulation may have any suitable characteristic as may serve a particular implementation. For example, the acoustic stimulation may include a relatively low frequency tone burst (e.g., a 125 Hz tone burst).

As another example, evoked response management facility 302 may direct cochlear implant 108 and receiver 114 to concurrently apply electrical stimulation and acoustic stimulation to the patient.

Evoked response management facility 302 may determine whether an evoked response occurs in response to the stimulation (i.e., the electrical and/or acoustic stimulation) in any suitable manner. For example, evoked response management facility 302 may use one or more electrodes to monitor for and record the evoked response. For example, a cochlear response (e.g., cochlear microphonics) may be recorded using one or more electrodes positioned within the cochlea (e.g., one or more of electrodes 112), one or more electrodes positioned within the round window, and/or one or more electrodes positioned at any other suitable location relatively near the cochlea. Likewise, a neural response (e.g., an auditory nerve response and/or a compound action potential) may be recorded using one or more electrodes positioned within or near the cochlea. It will be recognized that the electrode(s) used to record the evoked response may be disposed on a lead that has been inserted into the cochlea (e.g., electrode array 110), on a fly lead that has been positioned at any other suitable location within the patient, or on any other lead as may serve a particular implementation.

In some examples, one or more electrodes located external to the patient may be used to record an evoked response. For example, a brainstem response may be recorded using one or more non-invasive electrodes that have been affixed externally to the head of the patient.

In some examples, evoked response management facility 302 may use a microphone configured to be located within the ear canal of the patient to detect and record an evoked response (e.g., one or more otoacoustic emissions). These and other exemplary configurations that may be used to record evoked responses will be described in more detail below.

Evoked response management facility 302 may be configured to perform one or more predetermined actions in accordance with an evoked response that occurs in response to the stimulation (or in accordance with an evoked response not occurring in response to the stimulation). Exemplary predetermined actions that may be performed by evoked response management facility 302 will be described in more detail below.

Processing facility 304 may be configured to perform one or more processing operations associated with EAS system 100. For example, processing facility 304 may process audio signals detected by microphone 102 and direct cochlear implant 108 and/or receiver 114 to apply stimulation representative of the audio signals to the patient.

Storage facility 306 may be configured to maintain evoked response data 308 generated and/or utilized by evoked response management facility 302 and/or processing facility 304. In some examples, EAS sound processor 104 may store data representative of an evoked response within storage facility 306. Storage facility 306 may be configured to maintain additional or alternative data as may serve a particular implementation.

Various configurations that may be used to record various types of evoked responses will now be described. It will be recognized that the configurations described herein are merely illustrative of the various different configurations that may be used to record evoked responses in accordance with the systems and methods described herein.

Figure 4:
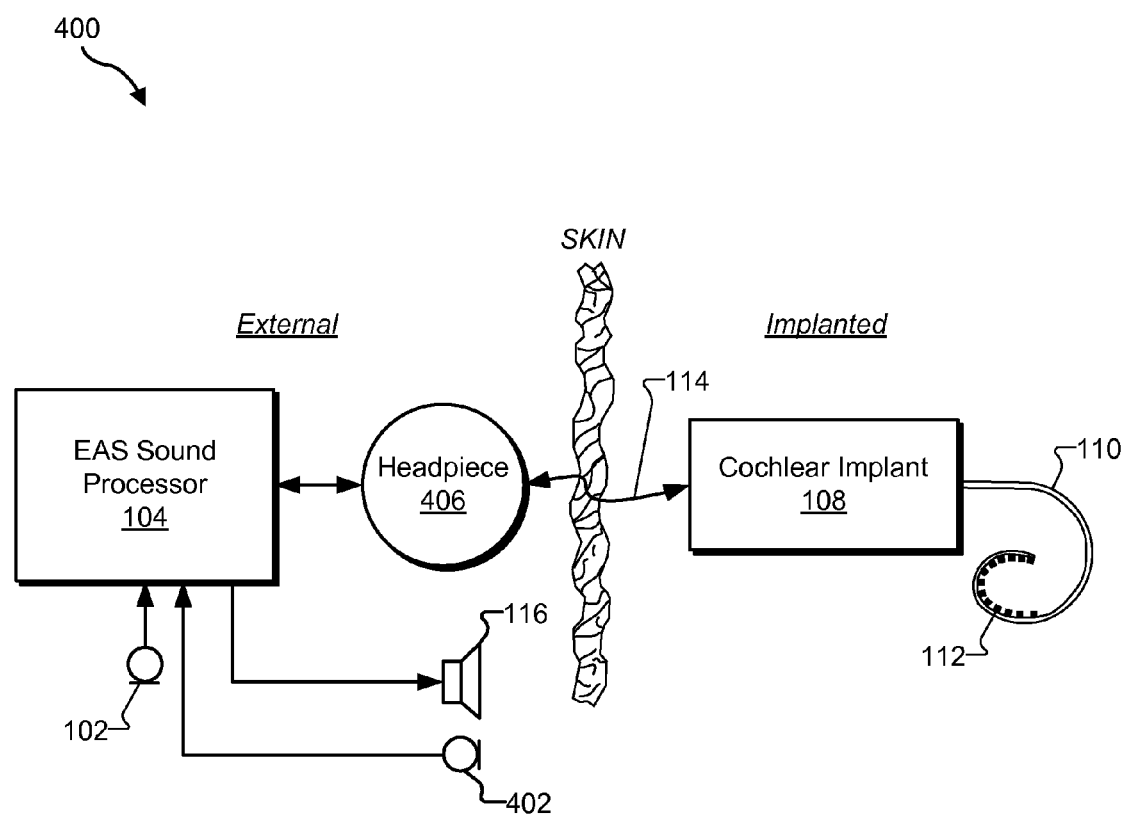
FIG. 4 illustrates an exemplary EAS system according to principles described herein.

FIG. 4 illustrates an exemplary EAS system 400 that may be used to record an evoked response in accordance with the systems and methods described herein. EAS system 400 is similar to EAS system 100, except that EAS system 400 further includes a second microphone 402 communicatively coupled to EAS sound processor 104. Microphone 402 may be configured to be located in an ear canal of the patient and may be used by EAS sound processor 104 to detect and record one or more otoacoustic emissions that occur in response to EAS system 400 applying electrical and/or acoustic stimulation to the patient. As used herein, "otoacoustic emissions" refer to sounds generated from within the inner ear in response to stimulation. In some examples, otoacoustic emissions may be indicative of inner ear health. For example, if EAS sound processor 104 does not detect a presence of otoacoustic emissions in response to stimulation, this may be indicative of a damaged or unhealthy inner ear.

EAS sound processor 104 may additionally or alternatively use one or more electrodes 112 included in electrode array 110 to record one or more evoked responses. Exemplary evoked responses that may be recorded using an electrode disposed within the cochlea, such as one of electrodes 112, include, but are not limited to, neural responses and one or more types of cochlear responses.

Figure 5:
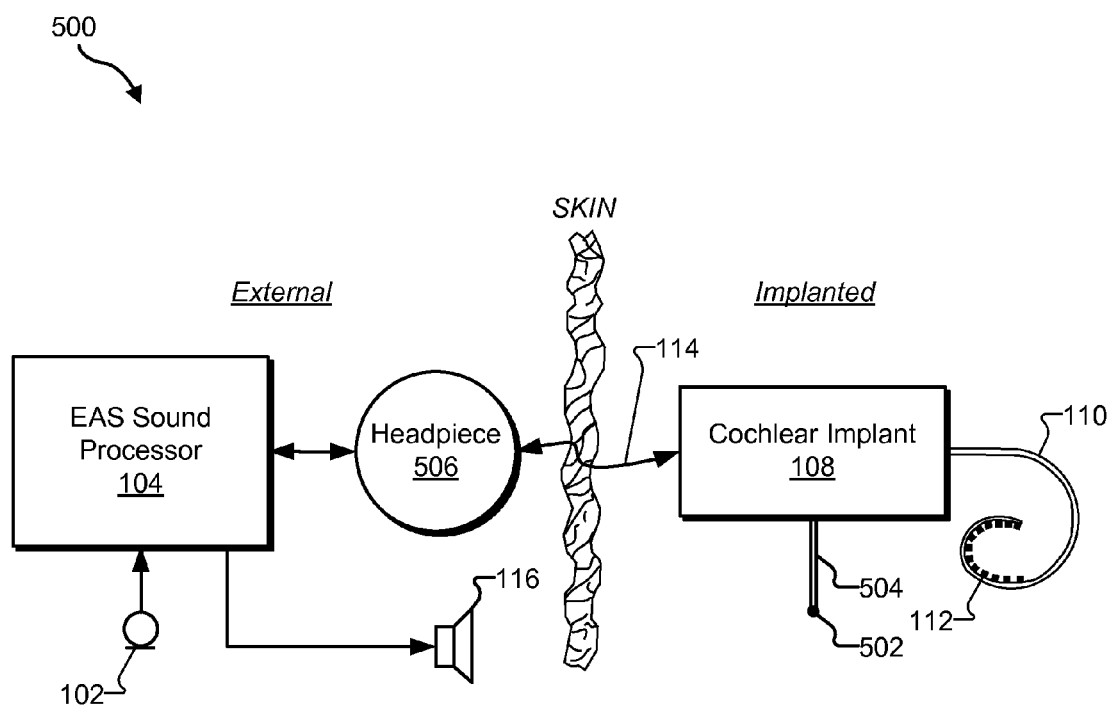
FIG. 5 illustrates an exemplary EAS system according to principles described herein.

FIG. 5 illustrates another exemplary EAS system 500 that may be used to record an evoked response in accordance with the systems and methods described herein. EAS system 500 is similar to EAS system 100, except that EAS system 500 further includes an extra-cochlear electrode 502 communicatively coupled to cochlear implant 108. While FIG. 5 shows extra-cochlear electrode 502 communicatively coupled to cochlear implant 108, it will be recognized that extra-cochlear electrode 502 may alternatively be coupled to EAS sound processor 104.

Extra-cochlear electrode 502 may include any type of electrode not located within the cochlea. For example, extra-cochlear electrode 502 may include a ring electrode, an electrode configured to be positioned within the round window, a stapedius electrode configured to be in communication with the stapedius muscle (i.e., coupled to the stapedius muscle and/or the stapedius tendon), and/or any other suitable electrode. In some examples, extra-cochlear electrode 502 is disposed on a lead 504 communicatively coupled to cochlear implant 108. Alternatively, extra-cochlear electrode 502 may be disposed on a portion of electrode array 110 that is not located within the cochlea.

In some examples, the use of an extra-cochlear electrode, such as extra-cochlear electrode 502, may allow for a "normalized" evoked response to be recorded while electrode array 110 is inserted during surgery. In other words, a surgeon may know that changes in evoked responses recorded with extra-cochlear electrode 502 are due to real changes in the source of the evoked responses as opposed to being due to changes in the relative position of electrode array 110 with respect to the source of the evoked responses.

In cases where the extra-cochlear electrode 502 is a stapedius electrode, EAS sound processor 104 may use the stapedius electrode to record a stapedius response associated with the stapedius muscle. As used herein, a "stapedius response" refers to an evoked response generated when the stapedial muscle contracts in response to stimulation (e.g., electrical stimulation at or above a most comfortable level ("M level") associated with the patient). EAS sound processor 104 may set a maximum power output ("MPO") for the acoustic stimulation based on the stapedius response and/or perform any other action in accordance with the stapedius response as may serve a particular implementation.

Various predetermined actions that may be performed by EAS sound processor 104 in accordance with an evoked response (or in accordance with a lack of an occurrence of an evoked response) will now be described. It will be recognized that the predetermined actions described herein are merely illustrative of the many different types of predetermined actions that may be performed in accordance with an evoked response.

In some examples, EAS sound processor 104 may set (e.g., adjust) one or more control parameters governing operation of EAS sound processor 104 and/or cochlear implant 108 in accordance with an evoked response that occurs in response to stimulation provided by EAS system 100.

Figure 6:
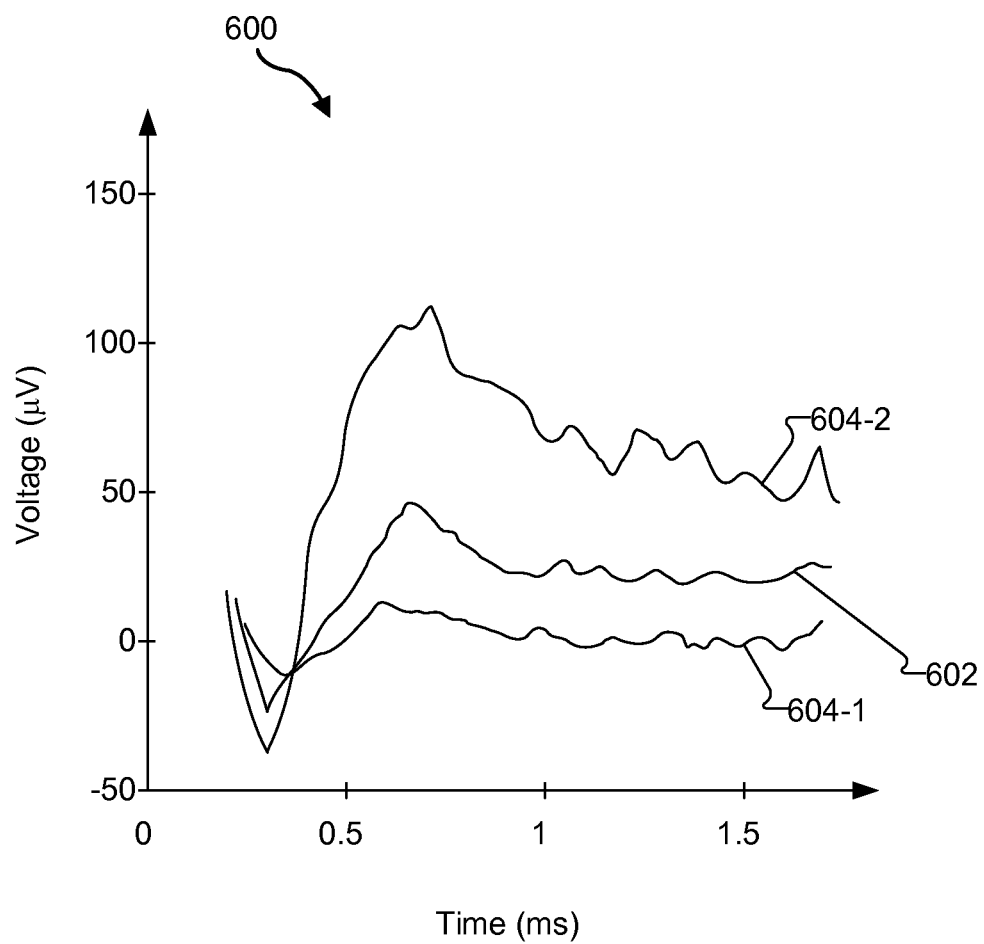
FIG. 6 shows an exemplary baseline response and two possible evoked responses according to principles described herein.

For example, EAS sound processor 104 may record an evoked response that occurs in response to electrical and/or acoustic stimulation and compare the evoked response to a baseline response and/or one or more previously recorded evoked responses. As used herein, a "baseline response" refers to some type of fixed evoked response that a clinician may consider to be normal, acceptable, and/or desirable. To illustrate, FIG. 6 shows an exemplary baseline response 602 and two possible evoked responses 604-1 and 604-2 that may occur in response to stimulation provided by EAS system 100. As shown, evoked response 604-1 is less than baseline response 602 (i.e., evoked response 604-1 has a steady state amplitude that is less than a steady state amplitude of baseline response 602). Conversely, evoked response 604-2 is greater than baseline response 602 (i.e., evoked response 604-2 has a steady state amplitude that is greater than a steady state amplitude of baseline response 602).

If the evoked response (e.g., evoked response 604-1) differs from the baseline response (e.g., baseline response 604-2) and/or the one or more previously recorded evoked responses (e.g., if the evoked response is not within a predetermined range of the baseline response and/or the one or more previously recorded evoked responses), EAS sound processor 104 may adjust one or more control parameters governing an operation of EAS sound processor 104 and/or cochlear implant 108 (e.g., by increasing an amplitude and/or intensity level of the stimulation provided by EAS system 100 and/or adjusting one or more other characteristics of the stimulation).

EAS sound processor 104 may additionally or alternatively provide one or more notifications to the patient and/or another user in accordance with an evoked response that occurs in response to stimulation provided by EAS system 100.

For example, if an evoked response is not within a predetermined range of a baseline response and/or one or more previously recorded evoked responses, EAS sound processor 104 may provide the patient and/or another user with a notification. The notification may be an audible alert (e.g., one or more beeps), a visible alert (e.g., a flashing of an LED), a text-based alert, and/or any other type of notification as may serve a particular implementation. The patient and/or other user may then take appropriate action.

EAS sound processor 104 may additionally or alternatively evaluate a residual hearing status of the patient in accordance with an evoked response that occurs in response to stimulation provided by EAS system 100. A variety of different factors may affect a residual hearing status of a patient. For example, wax buildup in the ear, infection, sickness, patient age, and/or any other factor may temporarily and/or permanently affect a residual hearing status of the patient.

To evaluate the residual hearing status of the patient, EAS sound processor 104 may compare the evoked response to a previously recorded evoked response and determine, based on a comparison, that the patient's residual hearing is changing (e.g., deteriorating). In response, EAS sound processor 104 may notify the patient and/or another user, automatically adjust one or more control parameters governing an operation of EAS system 100 (e.g., by increasing an amplitude and/or intensity level of stimulation being provided to the user), and/or take any other action as may serve a particular implementation.

As an example, a patient may get an infection that negatively affects the patient's residual hearing. EAS sound processor 104 may detect this deterioration in the patient's residual hearing in accordance with one or more evoked responses recorded by EAS sound processor 104 and increase an intensity level of the acoustic stimulation being provided by way of receiver 114. Subsequently, the infection may go away. EAS sound processor 104 may detect this by detecting an increase in amplitude of one or more evoked responses recorded by EAS sound processor 104. In response, the intensity level of the acoustic stimulation may be set (e.g., decreased) to the level it was prior to the infection.

In some examples, based on the residual hearing status as determined by EAS sound processor 104, a clinician or other user may decide to provide further treatment to the patient. For example, the clinician may decide to apply systemic steroids if a drop in residual hearing is detected.

In some examples, EAS sound processor 104 may evaluate the residual hearing status by using the evoked response to measure a two-tone interaction phenomenon that occurs within the patient. When two or more tones are simultaneously presented to the cochlea, tones not originally contained in the stimulus can be generated due to active non-linear processes in the cochlea. These measurable back-propagated responses are called distortion products and are considered to be indicative of healthy cochlear activity. They can be recorded acoustically from a patient's ear canal (e.g., otoacoustic emissions) or as electrical potentials from the neurons of the auditory pathway. Two-tone inhibition (i.e., a decrease in response to one tone in the presence of the second tone) is another phenomenon that occurs in part, due to cochlear non-linearity and can be measured using evoked responses.

EAS sound processor 104 may additionally or alternatively use the evoked response to determine one or more optimal crossover frequencies associated with the patient. As used herein, a "crossover frequency" refers to a boundary frequency that separates frequencies represented to the patient by acoustic stimulation and frequencies represented to the patient by electrical stimulation. For example, EAS sound processor 102 may determine that acoustic stimulation evokes robust hair cell and neural responses until 450 Hz. This frequency may therefore be designated as the crossover frequency (i.e., the apical-most electrode can start providing electrical stimulation around that frequency).

EAS sound processor 104 may additionally or alternatively use the evoked response to detect ectopic stimulation within the patient. As used herein, "ectopic" stimulation refers to abnormal stimulation that EAS system 100 may be providing to the patient. Ectopic stimulation may be indicated by equal masking on both sides of an electrode without reduction on one side. An evoked response may be indicative of ectopic stimulation in any suitable manner. For example, an irregular evoked response may be indicative of ectopic stimulation.

EAS sound processor 104 may additionally or alternatively use the evoked response to monitor for possible nerve regeneration within the patient. Nerve regeneration may cause changes in evoked responses over time (e.g., the amplitude of evoked responses may gradually increase over time). Hence, if EAS sound processor 104 detects a gradual increase in amplitude of evoked responses over time, this may be indicative of nerve regeneration. In some examples, EAS sound processor 104 may notify the patient and/or another user of the gradual increase and/or of the possible nerve regeneration, adjust one or more stimulation parameters accordingly, and/or take any other action based on the gradual increase as may serve a particular implementation.

EAS sound processor 104 may additionally or alternatively use the evoked response to assess (e.g., detect, characterize, etc.) tinnitus of cochlear origin in the patient. This may be performed in any suitable manner.

EAS sound processor 104 may additionally or alternatively use the evoked response to detect (i.e., characterize) an interaction between acoustic stimulation and electrical stimulation provided by EAS system 100. The acoustic and electrical stimulation provided by EAS system 100 may sometimes negatively interact with each other, thereby degrading the listening experience of an EAS patient. For example, the electrical stimulation provided by EAS system 100 may have a suppressive effect on the acoustic stimulation provided by EAS system 100 (e.g., by preventing the neurons in the apical region of the cochlea from responding to the acoustic stimulation). Likewise, the acoustic stimulation provided by EAS system 100 may have a suppressive interactive effect on the electrical stimulation provided by EAS system 100. Use of evoked responses to characterize an interaction between acoustic stimulation and electrical stimulation provided by EAS system 100 is described more fully in the above-referenced U.S. Provisional Patent Application No. 61/614,129.

EAS sound processor 104 may additionally or alternatively use the evoked response to assist in placement of electrode array 110 during an implantation procedure (i.e., surgery). For example, EAS sound processor 104 may record the evoked response during an implantation procedure in which electrode array 110 is inserted into the patient and determining, based on the evoked response, that the electrode array should be repositioned within the patient. For example, the evoked response may be abnormally low in amplitude. This may indicate that the electrode array 110 is not properly positioned within the cochlea. EAS sound processor 104 may provide a notification of this to the surgeon, who may adjust a positioning of electrode array 110 accordingly.

In some examples, EAS sound processor 104 may determine that an evoked response does not occur in response to stimulation provided by EAS system 100. EAS sound processor 104 may accordingly notify the patient, adjust one or more stimulation parameters, and/or perform one or more other actions as may serve a particular implementation.

For example, EAS sound processor 104 may determine that a compound action potential does not occur in response to stimulation provided by EAS system 100. This may be indicative of auditory neuropathy, and may affect how EAS system 100 is to be fitted to the patient (e.g., EAS system 100 may be programmed to provide only electrical stimulation if residual hearing is no longer of consequence to the patient).

Figure 7:
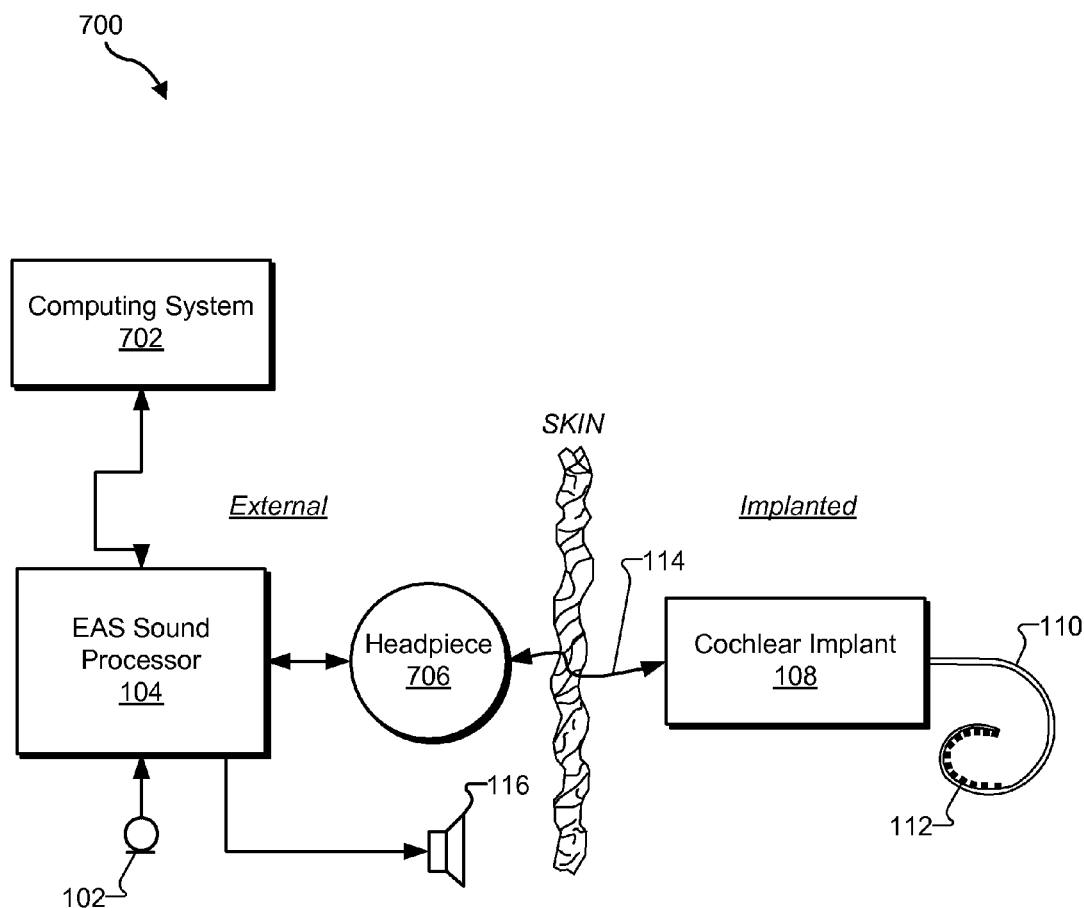
FIG. 7 shows an exemplary configuration in which a computing system is communicatively coupled to an EAS sound processor according to principles described herein.

In some examples, EAS sound processor 104 may transmit data representative of the evoked response to a computing system for further processing. To illustrate, FIG. 7 shows an exemplary configuration 700 in which a computing system 702 is communicatively coupled to EAS sound processor 104. Computing system 702 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. In some examples, computing system 702 may provide one or more graphical user interfaces ("GUIs") (e.g., by presenting the one or more GUIs by way of a display screen) with which a clinician or other user may interact.

EAS sound processor 104 may transmit data representative of an evoked response to computing system 702. Computing system 702 may perform any suitable action (including any of the predetermined actions described herein) based on the data representative of the evoked response. For example, computing system 702 may present a graph representative of the evoked response by way of a display screen, provide one or more recommendations in accordance with the evoked response (e.g., one or more recommendations with respect to setting one or more stimulation parameters that govern EAS system 100), and/or perform any other suitable action as may serve a particular implementation.

EAS sound processor 104 may additionally or alternatively determine a source (e.g., a location within the cochlea) of one or more evoked responses. This may facilitate identification of one or more regions of properly functioning hair cells, identification of one or more acoustic dead regions for purposes of determining crossover frequencies, and/or any other action as may serve a particular implementation.

To illustrate, EAS sound processor 104 may direct receiver 114 to apply a constant level acoustic stimulus to the patient. While the acoustic stimulus is being applied, EAS sound processor 104 may use multiple electrodes 112 included in electrode array 110 to monitor for and record evoked responses (e.g., cochlear responses) that occur in response to the acoustic stimulus. EAS sound processor 104 may then differentially compare the evoked responses and determine which evoked response has the greatest amplitude. In some examples, the electrode that records the evoked response that has the greatest amplitude corresponds to a region within the cochlea that is the source of the evoked responses.

In some examples, EAS sound processor 104 may automatically determine the source of the evoked responses (e.g., by identifying a maximum value included in an evoked response map similar to evoked response map 702). EAS sound processor 104 may then take any appropriate action based on this determination (e.g., notify the patient or another user, adjust one or more control parameters, etc.).

Figure 8:
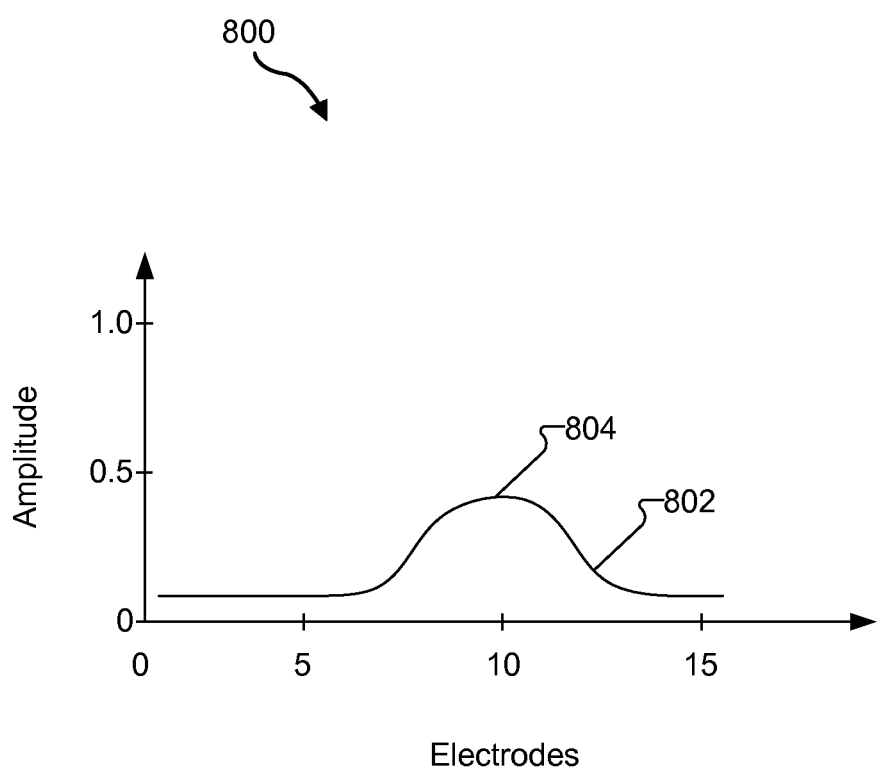
FIG. 8 shows an exemplary graph that may be presented by a computing system according to principles described herein.

In some examples, EAS sound processor 104 may transmit data representative of the evoked responses to computing system 702. Computing system 702 may then present a graph of the amplitudes of the evoked responses across the different electrodes (i.e., an evoked response map) to facilitate identification by a clinician or other user of the source of the evoked responses. For example, FIG. 8 shows an exemplary graph 800 that may be presented by computing system 702 by way of a display screen associated with computing system 702. As shown, graph 800 includes an evoked response map 802 that plots the amplitude of the evoked responses measured by a plurality of electrodes. In the particular example of FIG. 8, evoked response map 802 includes a peak 804 centered at electrode 10. By viewing graph 800, a clinician may readily ascertain that the source of the evoked responses is a location within the cochlea that corresponds to the position of electrode 10 (e.g., a location associated with a frequency of approximately 750 Hz).

In some examples, EAS sound processor 104 may periodically (e.g., every time EAS sound processor 104 is powered on) elicit and record a plurality of evoked responses over a period of time during normal use of EAS system 100 by the patient. EAS sound processor 104 may then perform one or more predetermined actions in accordance with the plurality of evoked responses. For example, the plurality of evoked responses, taken as a whole, may be indicative of a change in a residual hearing status of the patient. EAS sound processor 104 may accordingly adjust one or more stimulation parameters and/or take any other suitable predetermined action as may serve a particular implementation.

Figure 9:
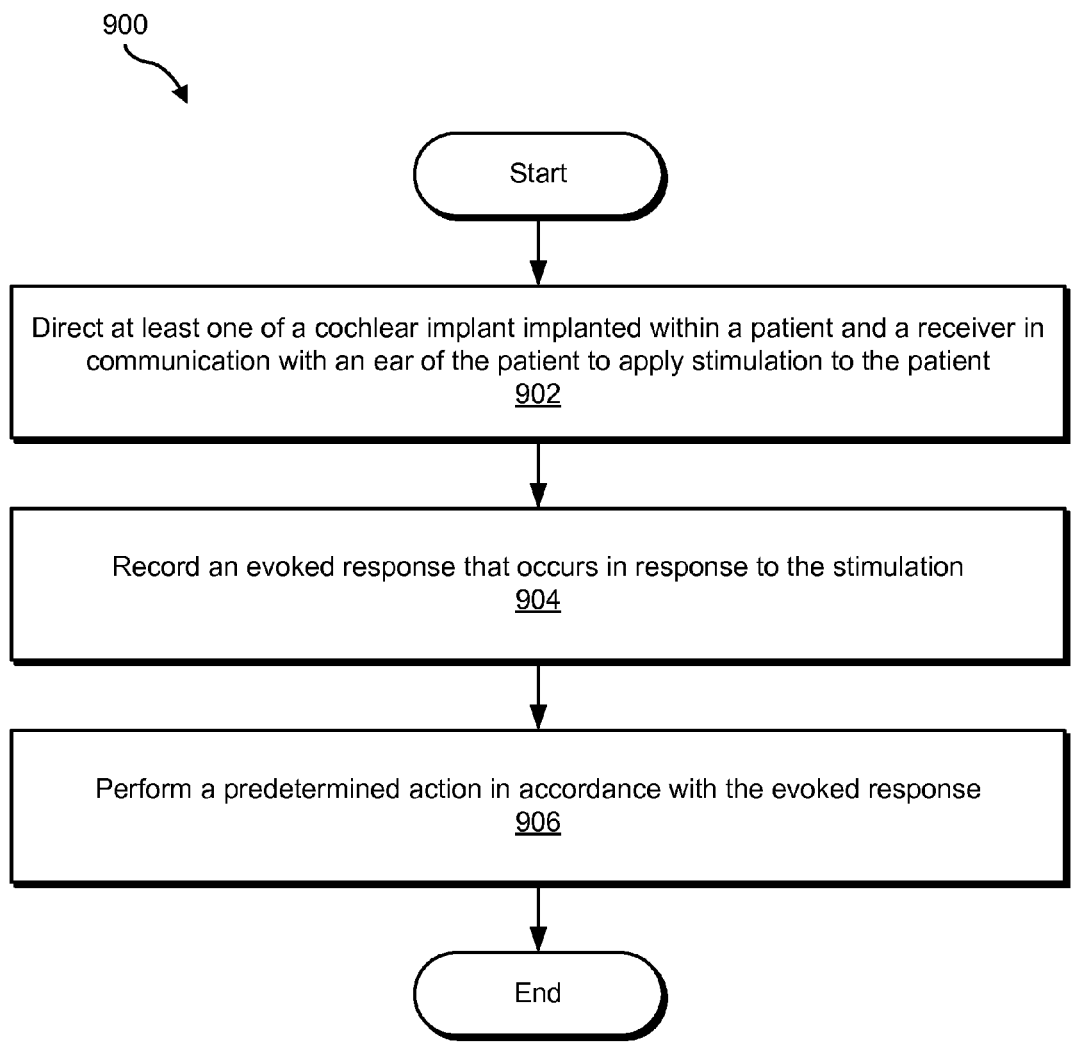
FIG. 9 illustrates an exemplary EAS method according to principles described herein.

FIG. 9 illustrates an exemplary EAS method 900. While FIG. 9 illustrates exemplary steps according to one embodiment, other embodiments may omit, add to, reorder, and/or modify any of the steps shown in FIG. 9. One or more of the steps shown in FIG. 9 may be performed by EAS sound processor 104 and/or any implementation thereof.

In step 902, an EAS sound processor directs at least one of a cochlear implant implanted within a patient and a receiver in communication with an ear of the patient to apply stimulation to the patient. Step 902 may be performed in any of the ways described herein.

In step 904, the EAS sound processor records an evoked response that occurs in response to the stimulation. Step 904 may be performed in any of the ways described herein.

In step 906, the EAS sound processor performs a predetermined action in accordance with the evoked response. Step 906 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 10:
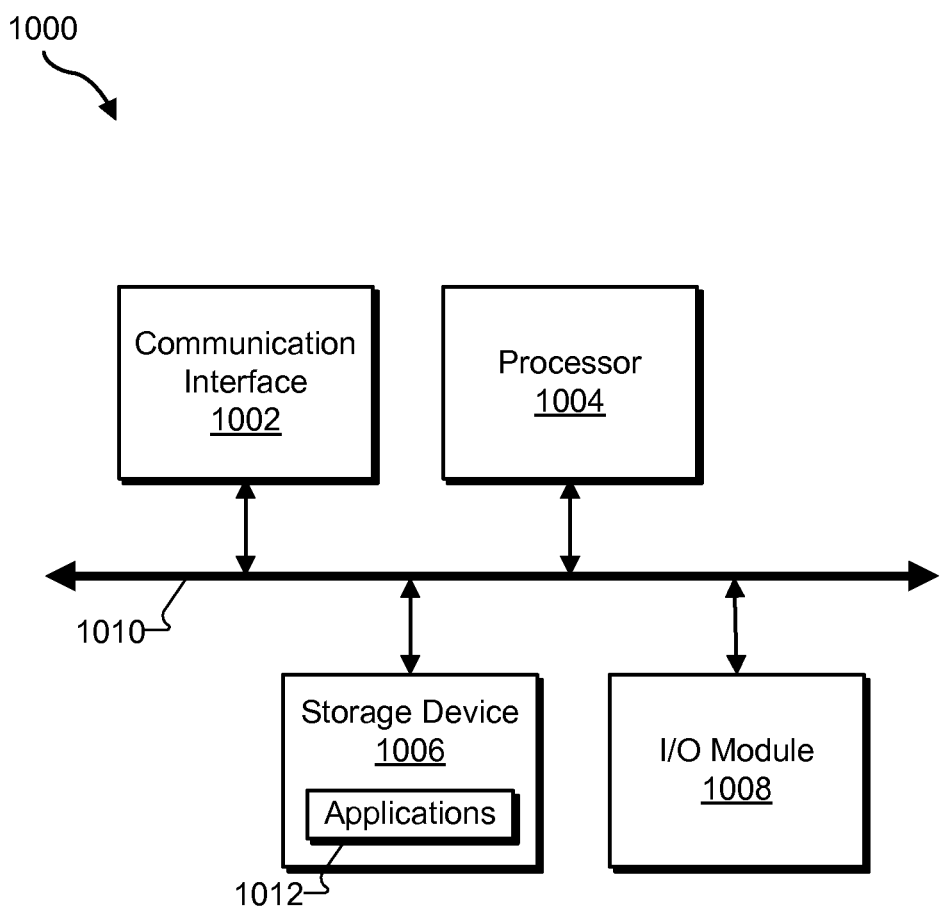
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data or interpreting, executing, and/or directing execution of one or more of the instructions, processes, and/or operations described herein. Processor 1004 may direct execution of operations in accordance with one or more applications 1012 or other computer-executable instructions such as may be stored in storage device 1006 or another computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities and/or systems described herein may be implemented by or within one or more components of computing device 1000. For example, one or more applications 1012 residing within storage device 1006 may be configured to direct processor 1004 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
an electro-acoustic stimulation ("EAS") sound processor configured to be located external to a patient;
a cochlear implant communicatively coupled to the EAS sound processor and configured to be implanted within the patient;
an electrode array communicatively coupled to the cochlear implant and configured to be located within a cochlea of the patient; and
a receiver communicatively coupled to the EAS sound processor and configured to be in communication with an ear of the patient;
wherein the EAS sound processor
directs, during a period of time after an implantation procedure in which the electrode array is inserted into the patient, at least one of the cochlear implant and the receiver to apply stimulation to the patient,
records an evoked response that occurs in response to the stimulation,
compares the evoked response to an additional evoked response previously recorded by the EAS sound processor during the period of time,
determines, based on the comparison, that a residual hearing status of the patient has deteriorated during the period of time,
increases, in response to the determination that the residual hearing status of the patient has deteriorated during the period of time, an intensity level of acoustic stimulation provided by the EAS sound processor by way of the receiver in order to present audio content to the patient subsequent to the period of time, determines that the residual hearing status of the patient improves subsequent to the period of time, and decreases, in response to the determination that the residual hearing status of the patient improves subsequent to the period of time, the intensity level of the acoustic stimulation provided by the EAS sound processor.

2. The system of claim 1, wherein the stimulation comprises electrical stimulation, and wherein the EAS sound processor directs the cochlear implant to apply the electrical stimulation to the patient by way of at least one electrode included in the electrode array.

3. The system of claim 1, wherein the stimulation comprises acoustic stimulation, and wherein the EAS sound processor directs the receiver to apply the acoustic stimulation to the patient.

4. The system of claim 1, wherein the stimulation comprises electrical stimulation and acoustic stimulation, and wherein the EAS sound processor directs the cochlear implant to apply the electrical stimulation to the patient by way of at least one electrode included in the electrode array and the receiver to apply the acoustic stimulation to the patient, wherein the electrical stimulation and the acoustic stimulation are concurrently applied to the patient.

5. The system of claim 1, wherein the EAS sound processor records the evoked response using an electrode included in the electrode array.

6. The system of claim 1, further comprising an extra-cochlear electrode communicatively coupled to at least one of the cochlear implant and the EAS sound processor, wherein the EAS sound processor records the evoked response using the extra-cochlear electrode.

7. The system of claim 1, further comprising:
a microphone communicatively coupled to the EAS sound processor and configured to be located in an ear canal of the patient;
wherein
the evoked response comprises one or more otoacoustic emissions, and
the EAS sound processor records the one or more otoacoustic emissions using the microphone configured to be located in the ear canal of the patient.

8. The system of claim 1, further comprising:
a stapedius electrode configured to be in communication with a stapedius muscle of the patient;
wherein
the evoked response comprises a stapedius response associated with the stapedius muscle, and
the EAS sound processor records the stapedius response using the stapedius electrode.

9. The system of claim 1, further comprising:
a computing system communicatively coupled to the EAS sound processor and configured to be located external to the patient;
wherein the EAS sound processor transmits data representative of the evoked response to the computing system.

10. The system of claim 1, wherein the EAS sound processor determines a source of the evoked response.

11. The system of claim 1, wherein the EAS sound processor sets one or more control parameters governing an operation of at least one of the EAS sound processor and the cochlear implant in accordance with the evoked response.

12. The system of claim 1, wherein the EAS sound processor further:

compares the evoked response to a baseline response; and
provides at least one of the patient and another user with a notification if the evoked response is not within a predetermined range of the baseline response.

13. The system of claim 1, wherein the EAS sound processor uses the evoked response to determine an optimal crossover frequency associated with the patient.

14. The system of claim 1, wherein the EAS sound processor:
records another evoked response during the implantation procedure in which the electrode array is inserted into the patient; and
determines, based on the another evoked response, that the electrode array should be repositioned within the patient.

15. The system of claim 1, wherein the EAS sound processor notifies at least one of the patient and another user that the residual hearing status of the patient has deteriorated.

16. A system comprising:
an electro-acoustic stimulation ("EAS") sound processor configured to be located external to a patient;
a cochlear implant communicatively coupled to the EAS sound processor and configured to be implanted within the patient;
an electrode array communicatively coupled to the cochlear implant and configured to be located within a cochlea of the patient; and
a receiver communicatively coupled to the EAS sound processor and configured to be in communication with an ear of the patient;
wherein the EAS sound processor
directs, during a period of time after an implantation procedure in which the electrode array is inserted into the patient, at least one of the cochlear implant and the receiver to apply stimulation to the patient,
records an evoked response that occurs in response to the stimulation,
compares the evoked response to an additional evoked response previously recorded by the EAS sound processor during the period of time,
determines, based on the comparison, that a residual hearing status of the patient has improved during the period of time, and
automatically decreases, in response to the determination that the residual hearing status of the patient has improved during the period of time, an intensity level of acoustic stimulation provided by the EAS sound processor by way of the receiver in order to present audio content to the patient subsequent to the period of time.

17. The system of claim 16, wherein the EAS sound processor:
provides, in response to the determination that the residual hearing status of the patient has improved, a notification to a user that the residual hearing status of the patient has improved.

18. The system of claim 16, wherein the EAS sound processor:
determines that the residual hearing status of the patient deteriorates subsequent to the period of time, and
increases, in response to the determination that the residual hearing status of the patient deteriorates subsequent to the period of time, the intensity level of the acoustic stimulation provided by the EAS sound processor.

19. A method comprising:
directing, by an electro-acoustic stimulation ("EAS") sound processor, at least one of a cochlear implant implanted within a patient and communicatively coupled to an electrode array that is located within a cochlea of the patient and a receiver in communication with an ear of the patient to apply stimulation to the patient during a period of time after an implantation procedure in which the electrode array is inserted into the patient;
recording, by the EAS sound processor, an evoked response that occurs in response to the stimulation; and
comparing, by the EAS sound processor, the evoked response to an additional evoked response previously recorded by the EAS sound processor during the period of time;
determining, by the EAS sound processor based on the comparing, that a residual hearing status of the patient has deteriorated during the period of time;
increasing, by the EAS sound processor in response to the determination that the residual hearing status of the patient has deteriorated during the period of time, an intensity level of acoustic stimulation provided by the EAS sound processor by way of the receiver in order to present audio content to the patient subsequent to the period of time;
determining, by the EAS sound processor, that the residual hearing status of the patient improves subsequent to the period of time; and
decreasing, by the EAS sound processor in response to the determining that the residual hearing status of the patient improves subsequent to the period of time, the intensity level of the acoustic stimulation provided by the EAS sound processor.

20. The method of claim 19, further comprising notifying, by the EAS sound processor, at least one of the patient and another user that the residual hearing status of the patient has deteriorated.

* * * * *